(12) United States Patent
Mori et al.

(10) Patent No.: US 11,052,034 B2
(45) Date of Patent: Jul. 6, 2021

(54) COSMETIC FOR CORRECTING BUMPS AND DIPS

(71) Applicants: NIKKO CHEMICALS CO., LTD., Tokyo (JP); COSMOS TECHNICAL CENTER CO., LTD., Tokyo (JP); TOAGOSEI CO., LTD., Tokyo (JP)

(72) Inventors: Rikako Mori, Tokyo (JP); Shunsuke Yamaguchi, Tokyo (JP); Takamasa Satonaka, Aichi (JP)

(73) Assignees: NIKKO CHEMICALS CO., LTD., Tokyo (JP); COSMOS TECHNICAL CENTER CO., LTD., Tokyo (JP); TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 16/304,318

(22) PCT Filed: May 25, 2017

(86) PCT No.: PCT/JP2017/019474
§ 371 (c)(1),
(2) Date: Nov. 26, 2018

(87) PCT Pub. No.: WO2017/204281
PCT Pub. Date: Nov. 30, 2017

(65) Prior Publication Data
US 2019/0133915 A1  May 9, 2019

(30) Foreign Application Priority Data
May 27, 2016 (JP) .............................. JP2016-106166

(51) Int. Cl.
| | |
|---|---|
| *A61K 8/81* | (2006.01) |
| *A61Q 1/02* | (2006.01) |
| *A61Q 1/00* | (2006.01) |
| *A61K 8/02* | (2006.01) |
| *A61K 8/29* | (2006.01) |
| *A61Q 19/08* | (2006.01) |

(52) U.S. Cl.
CPC ............ *A61K 8/8152* (2013.01); *A61K 8/025* (2013.01); *A61K 8/29* (2013.01); *A61K 8/8147* (2013.01); *A61Q 1/00* (2013.01); *A61Q 1/02* (2013.01); *A61Q 19/08* (2013.01); *A61K 2800/412* (2013.01); *A61K 2800/43* (2013.01); *A61K 2800/546* (2013.01)

(58) Field of Classification Search
CPC ........ A61K 8/8152; A61K 8/025; A61K 8/29; A61K 8/8147; A61K 2800/412; A61K 2800/43; A61K 2800/546; A61Q 1/00; A61Q 1/02; A61Q 19/08
See application file for complete search history.

(56) References Cited

U.S. PATENT DOCUMENTS

| | | | | |
|---|---|---|---|---|
| 6,045,783 A | * | 4/2000 | Macchio .............. | A61K 8/8147 424/401 |
| 6,139,829 A | * | 10/2000 | Estrin ................. | A61K 8/8158 424/78.03 |
| 8,415,433 B2 | | 4/2013 | Matsuzaki et al. | |
| 9,056,800 B2 | | 6/2015 | Gotou et al. | |
| 2006/0165736 A1 | * | 7/2006 | Kito ......................... | A61K 8/06 424/401 |
| 2010/0069592 A1 | * | 3/2010 | Matzuaki .............. | C08F 290/04 526/287 |
| 2011/0046329 A1 | * | 2/2011 | Gotou ....................... | C08F 4/40 526/229 |
| 2013/0243836 A1 | * | 9/2013 | Tanner ................. | A61K 8/0254 424/401 |
| 2016/0030328 A1 | * | 2/2016 | Mohammadi ....... | C08F 290/068 424/63 |

FOREIGN PATENT DOCUMENTS

| | | |
|---|---|---|
| CN | 101111223 A | 1/2008 |
| CN | 101926744 A | 12/2010 |
| CN | 103370042 A | 10/2013 |
| CN | 104114148 A | 10/2014 |
| FR | 2967056 A1 | 5/2012 |
| FR | 2983071 A1 | 5/2013 |
| FR | 2999909 A1 | 6/2014 |

(Continued)

OTHER PUBLICATIONS

International Search Report issued in connection with PCT/JP2017/019474, dated Aug. 29, 2017 (English translation).

(Continued)

*Primary Examiner* — Robert A Wax
*Assistant Examiner* — Olga V. Tcherkasskaya
(74) *Attorney, Agent, or Firm* — Biospark Intellectual Property Law

(57) ABSTRACT

A subject of the present invention is to provide a cosmetic for unevenness correction which has an excellent effect of concealing wrinkles and pores and correcting skin unevenness and has good compatibility with a makeup cosmetic. The present inventors have found that the cosmetic for unevenness correction which conceals wrinkles and pores and has good compatibility with a makeup cosmetic at the time of application can be easily provided by using a polyacrylate water-absorbing polymer having a specific water absorption capacity, but not a water-soluble macromolecule having a thickening effect commonly used in cosmetics, and they thus have completed the present invention. That is, the present invention provides a cosmetic for unevenness correction comprising the polyacrylate water-absorbing polymer which has an excellent effect of concealing wrinkles and pores, and the polyacrylate water-absorbing polymer has an average swollen particle size of 10 to 150 µm, an average dry particle size of 10 to 50 µm and a water absorbency of 5 to 50 g/g.

8 Claims, No Drawings

(56) References Cited

FOREIGN PATENT DOCUMENTS

| JP | 2000-007551 | A | 1/2000 |
| JP | 2002-179530 | A | 6/2002 |
| JP | 2004-210654 | A | 7/2004 |
| JP | 2004-331760 | A | 11/2004 |
| JP | 5786859 | B2 | 9/2015 |
| WO | 2008/015870 | A1 | 2/2008 |
| WO | 2012/023376 | A1 | 2/2012 |
| WO | 2012/033078 | A1 | 3/2012 |

OTHER PUBLICATIONS

Written Opinion of the International Searching Authority issued in connection with PCT/JP2017/019474, dated Aug. 29, 2017 (English translation).

Office Action issued in connection with Chinese patent application No. CN 201780032899.7, dated Jun. 16, 2020.

Notification of Decision to Grant a Patent issued in connection with French patent application No. FR 1754659, dated Jul. 24, 2020.

\* cited by examiner

COSMETIC FOR CORRECTING BUMPS AND DIPS

TECHNICAL FIELD

The present invention relates to a cosmetic for unevenness correction comprising a water-absorbing polymer which has an excellent effect of concealing wrinkles and pores.

BACKGROUND ART

Many women have trouble with wrinkles and pores, and conceal them by using makeup cosmetics. The effect of the makeup cosmetics depends on their optical properties such as the concealing effect and scattering effect of powders. Conventionally used techniques involving powders having high refractive index such as titanium oxide have high concealing power but have a problem that they result in an unnatural finish. In recent years, there has been a technique for concealing wrinkles without artificiality, for example, by incorporating methyl polysiloxane having a high degree of polymerization and a volatile oil solution and a translucent powder into an emulsion cosmetic for concealing wrinkles (Japanese Patent Laid-Open No. 2000-007551), but it is difficult to sufficiently correct wrinkles and pores. There has also been a technique for making wrinkles and pores invisible by forming a continuous film containing a powder in a layer thereof with a film forming agent so that the film has a specific surface roughness (Japanese Patent Laid-Open No. 2002-179530). In particular, silicone film forming agents can banish wrinkles by stretching wrinkles, and can be included into makeup bases to make makeup cosmetics to be applied thereon spread well. However, they have problems of poor usability such as sticky feeling or stretched feeling and restriction of muscular movement. Further, there has been a method for concealing skin unevenness by applying on the skin a cosmetic for concealing unevenness comprising a water-absorbing polymer having a water content of less than a saturated amount of water absorption and a binder and then contacting with the application site another cosmetic comprising a water-soluble ingredient that can swell the water-absorbing polymer (Japanese Patent Laid-Open No. 2004-210654). However, the method has a problem that it takes time and effort due to its two-step use and it requires a high content, i.e., 10% by mass or more of the water-absorbing polymer.

SUMMARY OF THE INVENTION

Problem to be Solved by the Invention

A subject of the present invention is to provide a cosmetic for unevenness correction which has an excellent effect of concealing wrinkles and pores and correcting skin unevenness and has good compatibility with a makeup cosmetic.

Means to Solve the Problem

The present inventors have found that a cosmetic for unevenness correction which conceals wrinkles and pores and has good compatibility with a makeup cosmetic can be easily provided by using a polyacrylate water-absorbing polymer having a specific water absorption capacity, and they thus have completed the present invention.

More specifically, the present invention relates to a cosmetic for unevenness correction having an excellent effect of concealing wrinkles and pores, characterized by comprising a polyacrylate water-absorbing polymer which has an average swollen particle size of 10 μm to 150 μm, an average dry particle size of 10 μm to 50 μm and a water absorbency of 5 g/g to 50 g/g.

Effects of the Invention

According to the present invention, a cosmetic for unevenness correction which has an excellent effect of concealing wrinkles and pores and has good compatibility with a makeup cosmetic can be provided.

MODE FOR CARRYING OUT THE INVENTION

The present invention will be now described in detail as follows.

The polyacrylate water-absorbing polymer used in the present invention (hereinafter also referred to as polyacrylate water-absorbing polymer of the present invention) is characterized by having an average swollen particle size of 10 μm to 150 μm, an average dry particle size of 10 μm to 50 μm and a water absorbency of 5 g/g to 50 g/g.

The average swollen particle size and average dry particle size in the present invention mean a volume-based median size of the polyacrylate water-absorbing polymer saturated and swollen with ion-exchanged water and a volume-based median size of the polyacrylate water-absorbing polymer dried in n-heptane solvent having 2 wt % of a emulsifier dissolved therein, respectively, as measured with laser diffraction-scattering type particle size distribution measuring device (for example, Microtrac MT-3000, manufactured by NIKKISO CO., LTD.).

The water absorbency of the polyacrylate water-absorbing polymer in the present invention is calculated from the following equation:

$$\text{Water absorbency} = [\text{weight upon water absorption (g)} - \text{dry weight (g)}] / \text{dry weight (g)}$$

wherein the weight upon water absorption is the weight after swollen with ion-exchanged water for 30 minutes or more; and the dry weight is the weight after dried at 150° C. for 60 minutes in a windless dryer.

The average swollen particle size of the polyacrylate water-absorbing polymer of the present invention is 10 μm to 150 μm, preferably 10 μm to 100 μm, and more preferably 15 μm to 60 μm. As for the average dry particle size, if it is less than 10 μm or more than 50 μm, the cosmetic tends to have a poor effect of unevenness correction of wrinkles and pores, and may have a poor use feeling and poor compatibility with the makeup cosmetic. In light of the above, the average dry particle size is preferably in the range of 10 μm to 40 μm, more preferably in the range of 10 μm to 30 μm, and still more preferably in the range of 10 μm to 25 μm.

When the water absorbency of the polyacrylate water-absorbing polymer of the present invention is less than 5 g/g or more than 50 g/g, the cosmetic tends to have a poor effect of unevenness correction of wrinkles and pores, and may also have poor compatibility with the makeup cosmetic. In light of the above, the water absorbency is preferably in the range of 10 g/g to 30 g/g, and more preferably in the range of 15 g/g to 30 g/g.

The polyacrylate water-absorbing polymer of the present invention is used in the neutralized form, and the neutralizing agent is not limited. The degree of neutralization may be from 10 mol % to 100 mol %, preferably from 30 mol % to 90 mol %, and more preferably from 40 mol % to 80 mol %.

The polyacrylate water-absorbing polymer of the present invention includes a polyacrylate water-absorbing polymer selected from ammonium polyacrylate, potassium polyacrylate and sodium polyacrylate.

The shape of the polyacrylate water-absorbing polymer particles of the present invention is not particularly limited, but may be an ellipsoidal shape or a spherical shape, or an irregular shape. From the viewpoint of good swellability with water, it is preferably an ellipsoidal or spherical polymer particle shape.

Polyacrylate polymers are generally classified into thickening polymers and water-absorbing polymers. The thickening polymers exhibit solubility in solvents and absorb water infinitely so that they exhibit a thickening effect in a concentration-dependent manner. The polyacrylate water-absorbing polymer of the present invention is a water-absorbing polymer. As the water-absorbing polymers, those used in hygienic materials such as disposable diapers and sanitary napkins are well known, and the water-absorbing polymers used in these applications have generally a high water absorbency of 50 g/g to 1000 g/g. In contrast, the polyacrylate water-absorbing polymer of the present invention has a relatively low water absorbency of 5 g/g to 50 g/g.

Examples of the polyacrylate water-absorbing polymer of the present invention include crosslinked (co)polymers derived from monomer(s) (mixture) comprising a hydrophilic vinyl monomer such as (meth)acrylic acid or salts thereof. Examples of the hydrophilic vinyl monomer include: vinyl monomers having a carboxyl group or (partially) alkali-neutralized products thereof such as crotonic acid, itaconic acid, maleic acid, fumaric acid, monobutyl itaconate, monobutyl maleate, cyclohexane dicarboxylic acid in addition to (meth)acrylic acid; vinyl monomers having an amino group or (partially) acid-neutralized products thereof, or (partially) quaternized products thereof such as N,N-dimethylaminoethyl (meth)acrylate, N,N-diethylaminoethyl (meth)acrylate, N,N-dimethylaminopropyl (meth)acrylate, N,N-dimethylaminopropyl (meth)acrylamide; N-vinylpyrrolidone, acryloyl morpholine; vinyl monomers having a phosphoric acid group or (partially) alkali-neutralized products thereof such as acid phosphooxyethyl methacrylate, acid phosphooxypropyl methacrylate, 3-chloro-2-acid phosphooxypropyl methacrylate; vinyl monomers having a sulfonic or phosphonic acid group or (partially) alkali-neutralized products thereof such as 2-(meth)acrylamide-2-methylpropanesulfonic acid, 2-sulfoethyl (meth)acrylate, 2-(meth)acryloyl ethanesulfonic acid, allyl sulfonic acid, styrenesulfonic acid, vinyl sulfonic acid, allyl phosphonic acid, vinyl phosphonic acid; nonionic hydrophilic monomers such as (meth)acrylamide, N,N-dimethylacrylamide, N-isopropyl acrylamide, N-methylol (meth)acrylamide, N-alkoxymethyl (meth)acrylamide, (meth)acrylonitrile, hydroxyethyl (meth)acrylate, hydroxypropyl (meth)acrylate, methoxypolyethylene glycol mono (meth)acrylate, and one or more of these may be used. (Meth)acrylic acid means acrylic acid and/or methacrylic acid. Other compounds prefixed with (meth) as above mentioned are also to be understood similarly.

Among these monomers, vinyl monomers having a carboxyl group and vinyl monomers having a sulfonic acid group and (partially) alkali-neutralized products thereof are preferred in that they have excellent polymerizability and provide polyacrylate water-absorbing polymers which have a high hydrophilicity, excellent water absorption and water retention performances, and the like. Particularly preferred monomers are (meth)acrylic acid, 2-(meth)acrylamide-2-methylpropanesulfonic acid. Thus, the polyacrylate water-absorbing polymer of the present invention is a polymer, more preferably a crosslinked polymer, comprising as a constituent monomer(s) a monomer(s) selected from acrylic acid, methacrylic acid, 2-acrylamido-2-methylpropanesulfonic acid, 2-methacrylamido-2-methylpropanesulfonic acid and salts thereof. The polyacrylate water-absorbing polymer of the present invention preferably comprises as a constituent monomer(s) a monomer(s) selected from acrylic acid, methacrylic acid and salts thereof.

From the viewpoint of water absorption performance, the amount of the hydrophilic vinyl monomer used is preferably 50% by mass or more, more preferably 70% by mass or more, and still more preferably 90% by mass or more, based on the total amount of the monomers constituting the polyacrylate water-absorbing polymer of the present invention (excluding the crosslinking agent as mentioned below). The upper limit of the amount of the hydrophilic vinyl monomer used is 100% by mass.

As a method for crosslinking the copolymer, any known method may be employed, but a method using a crosslinking agent is generally used. As the crosslinking agent, for example, a polyfunctional vinyl monomer having two or more radically polymerizable groups may be copolymerized with the hydrophilic vinyl monomer, or a polyfunctional compound having two or more groups which can be reacted with a functional group of the hydrophilic vinyl monomer may be used.

Examples of the polyfunctional vinyl monomer include di or tri(meth)acrylates of polyols such as polyethylene glycol di(meth)acrylate, polypropylene glycol di(meth)acrylate, glycerol tri(meth)acrylate, trimethylolpropane tri(meth)acrylate, trimethylolpropane ethylene oxide modified tri(meth)acrylate, bisamides such as methylenebis(meth)acrylamide, divinylbenzene and allyl (meth)acrylate, and one or more of these may be used.

Examples of the polyfunctional compound include polyfunctional epoxy compounds such as ethylene glycol diglycidyl ether and polyethylene glycol diglycidyl ether, polyfunctional amine compounds such as hexamethylenediamine and N,N'-dicinnamylidene-1,6-hexanediamine, and polyfunctional isocyanate compounds such as hexamethylene diisocyanate, dimethyl diphenylene diisocyanate and isophorone diisocyanate, and one or more of these may be used.

The amount of the crosslinking agent used may vary depending on the type of the crosslinking agent used and the like, but is preferably 0.1 mol % to 30 mol %, and more preferably from 0.5 mol % to 10 mol %, based on the total amount of the monomers constituting the polyacrylate water-absorbing polymer of the present invention excluding the crosslinking agent. As long as the amount of crosslinking agent used is in the range of 0.1 mol % to 30 mol %, the water absorbency can be adjusted to a suitable range.

The method for producing the polyacrylate water-absorbing polymer of the present invention is not particularly limited, but a known polymerization method such as solution polymerization, suspension polymerization, reverse phase suspension polymerization, dispersion polymerization, and bulk polymerization can be employed. Suspension polymerization, reverse phase suspension polymerization and dispersion polymerization are preferred in that they easily provide the polymer particles in a spherical shape, and reverse phase suspension polymerization is particularly preferred in that it is easy to stably produce the polyacrylate water-absorbing polymer. Those skilled in the art can adjust the average particle size and water absorbency of the polyacrylate water-absorbing polymer of the present invention as appropriate by regulating the type and amount of the monomers used, the type and amount of the dispersion stabilizer used at the time of polymerization, and polymerization conditions such as polymerization temperature and stirring conditions, and the like. For example, in the case of reverse phase suspension polymerization, generally, the particle size of the obtained polymer is smaller under higher stirring conditions and the particle size of the obtained polymer increases under lower stirring conditions. In addition, when the degree of crosslinking of the polyacrylate water-absorbing polymer is increased, the water absorbency decreases, whereas in the case of a polymer having a lower degree of crosslinking, the water absorbency increases. Specific examples of the polyacrylate water-absorbing polymer of the present invention include absorbent resin fine particles of Aron NT series (manufactured by Toagosei Co., Ltd.).

The polyacrylate water-absorbing polymer of the present invention can be used as a cosmetic for unevenness correction in the form of the formulation comprising the polymer alone or in combination with an ingredient(s) to be incorporated into cosmetics or by adding the cosmetic ingredient(s) to the polymer. In the cosmetic for unevenness correction of the present invention, the content of the polyacrylate water-absorbing polymer of the present invention is preferably 0.1% by mass to 10% by mass, and more preferably 0.1% by mass to 9.0% by mass. If this content is less than 0.1% by mass, the cosmetic may not be able to sufficiently exert an effect of concealing wrinkles and pores. If the content is more than 10% by mass, the cosmetic may lose flowability by excessively absorbing water, resulting in an unstable formulation.

Furthermore, the cosmetic for unevenness correction comprising a polyacrylate water-absorbing polymer which has an excellent effect of concealing wrinkles and pores according to the present invention can comprise any ingredient(s) appropriately selected from ingredients incorporated into usual cosmetics, depending on the intended type of cosmetic. Examples of these ingredient(s) include, but are not limited to, hydrocarbon oils such as liquid paraffin and petrolatum, vegetable oils and fats, waxes, synthetic ester oils, silicone oil phase components, higher alcohols, lower alcohols, fatty acids, thickeners, ultraviolet absorbers, powders, inorganic/organic pigments, color materials, various surfactants, polyhydric alcohols, saccharides, macromolecular compounds, physiologically active ingredients, transdermal absorption promoting agents, solvents, antioxidants, perfumes and various additives. Specifically, the cosmetic for unevenness correction can comprise inorganic powders such as titanium oxide, mica, hectorite, colcothar, montmorillonite, kaolin, smectite, talc, perlite, or iron oxide such as yellow iron oxide, red iron oxide or black iron oxide. Alternatively, the formulation comprising the polymer alone can be used in combination with a composition comprising a cosmetic ingredient(s), for example, by applying the formulation and then applying a cosmetic composition comprising an inorganic powder.

Examples of the cosmetic for unevenness correction of the present invention include, but are not particularly limited to, a basic skin care such as a skin lotion for unevenness correction, a serum for unevenness correction and an emulsion for unevenness correction, a makeup base for unevenness correction, and a makeup cosmetic such as a foundation for unevenness correction.

The present invention is based on the finding that the polyacrylate water-absorbing polymer having an average swollen particle size of 10 μm to 150 μm, an average dry particle size of 10 μm to 50 μm and a water absorbency of 5 g/g to 50 g/g has an excellent effect of concealing skin unevenness such as wrinkles and pores. Accordingly, the present invention provides a polyacrylate water-absorbing polymer for the cosmetic for unevenness correction which has an average swollen particle size of 10 μm to 150 μm, an average dry particle size of 10 μm to 50 μm and a water absorbency of 5 g/g to 50 g/g. The present invention also provides a skin irregularity correction agent or a cosmetic irregularity correction agent comprising a polyacrylate water-absorbing polymer which has an average swollen particle size of 10 μm to 150 μm, an average dry particle size of 10 μm to 50 μm and a water absorbency of 5 g/g to 50 g/g. Furthermore, the present invention provides a cosmetic for unevenness correction comprising this irregularity correction agent.

The present invention is also based on the finding that the above-mentioned predetermined polyacrylate water-absorbing polymer has good compatibility with a makeup cosmetic in addition to having an excellent effect of concealing skin unevenness such as wrinkles and pores. Accordingly, the present invention provides a makeup base comprising a polyacrylate water-absorbing polymer which has an average swollen particle size of 10 μm to 150 μm, an average dry particle size of 10 μm to 50 μm and a water absorbency of 5 g/g to 50 g/g. Furthermore, the present invention provides a cosmetic process for unevenness correction comprising applying this makeup base to irregular portions of the skin and then applying another cosmetic thereon.

Specific examples and preferred embodiments of the polyacrylate water-absorbing polymer used herein are as described above.

EXAMPLES

The present invention will be further specifically described with reference to following examples, but is not intended to be limited thereto. The contents are expressed in % by mass.

Production Example 1: Production of Polymer A

For the polymerization, a reactor equipped with a stirring mechanism consisting of a pitch paddle type stirring blade and two vertical baffles, and with a thermometer, a reflux condenser and a nitrogen inlet tube was used. This nitrogen inlet tube was branched to two tubes outside of the reactor one of which was used to feed nitrogen and the other of which was used to feed a polymerization catalyst via a pump. Further, the nitrogen inlet tube was connected to a wall surface of the reactor at almost the same height as the upper end of the stirring blade.

2.94 parts by mass of sorbitan monooleate (trade name "RHEODOL A0-10 V", manufactured by Kao Corporation) and 375.0 parts by mass of n-heptane as a polymerization solvent were charged into the reactor, and were mixed with stirring while keeping the temperature of the solution at 40° C. to prepare the oil phase. The oil phase was stirred at 40° C. for 30 minutes and then cooled to 15° C.

On the other hand, 100.0 parts by mass of acrylic acid, 9.7 parts by mass of polyethylene glycol diacrylate (trade name "ARONIX M-243", average molecular weight 425 g/mol, manufactured by Toagosei Co., Ltd.), 0.02 parts by mass of p-methoxyphenol and 82.4 parts by mass of ion-exchanged water were charged into another container, and the mixture was stirred to uniformly dissolve them. Furthermore, while cooling the mixture so as to keep the temperature at 40° C. or less, 73.1 parts by mass of 48% aqueous solution of potassium hydroxide was gradually added thereto to neutralize it (degree of neutralization: 45 mol %) to prepare a liquid monomer mixture.

After setting the rotation speed of the stirrer at 900 rpm, the prepared liquid monomer mixture was charged into the reactor to prepare a dispersion having the liquid monomer mixture dispersed in the oil phase. At this time, the internal temperature of the reactor was kept at 15° C. Nitrogen was blown into the dispersion to remove oxygen in the reactor. 1 hour and 30 minutes after charging the monomer mixture, an aqueous solution containing 0.09 parts by mass of sodium hydrosulfite and 3.0 parts by mass of ion-exchanged water was added thereto through an inlet provided at the top of the reactor. Three minutes later, a solution obtained by diluting 0.04 parts by mass of an 80% solution of cumene hydroperoxide (trade name "Percumyl H80", manufactured by NOF CORPORATION) with 3.0 parts by mass of n-heptane was fed through a nitrogen inlet tube via a pump. The solution was fed in 30 seconds. Immediately after the start of feeding, the internal temperature of the reactor increased, confirming that polymerization started. The increase in internal temperature peaked in about 40 seconds, at which time the temperature was 61.9° C. Then, the reaction liquid was cooled to 15° C. to obtain a dispersion of Polymer A.

Each of raw materials such as monomers, polymerization solvent, and polymerization initiator is commercially available industrial products and was used as received without treatment such as purification.

Further, the dispersion of Polymer A was heated to allow water contained in particles and heptane to be azeotropically distilled and thereby dehydrated to a dehydration rate of 95%, and then filtered to remove a heptane phase. Heptane was added at the same weight as the filtrate, stirred and then filtered. This procedure was repeated twice, and then the solvent was volatilized with a forced-air dryer to obtain a dry powder of Polymer A. In addition, scanning electron microscope (SEM) observation confirmed that the Polymer A was in the form of spherical particles.

Production Examples 2 to 10: Production of Polymers B to J

The same procedure as in Production Example 1 was carried out to obtain dry powders of Polymers B to J except that the swollen particle size was adjusted by regulating the stirring rotation number and the water absorbency was adjusted by changing the number of parts of the crosslinking agent, polyethylene glycol diacrylate (trade name "ARONIX M-243", manufactured by Toagosei Co., Ltd.). However, as a neutralizing agent, an aqueous sodium hydroxide solution or aqueous ammonia was used to vary the type of salts as appropriate. In addition, scanning electron microscope (SEM) observation confirmed that the Polymers B to J were in the form of spherical particles.

Example 1

The average particle size and water absorbency of the polyacrylate water-absorbing polymer were measured.
(1) Method for Measuring the Average Particle Size Preparation of a sample for measuring the average swollen particle size: The polyacrylate water-absorbing polymer was swollen with ion exchanged water for 30 minutes or more and was used as a measurement sample.

Preparation of a sample for measuring the average dry particle size: The polyacrylate water-absorbing polymer was dispersed for dehydration in n-heptane having 2 wt % of tetraglycerol polyricinoleate (trade name: CRS-75, manufactured by SAKAMOTO YAKUHIN KOGYO CO., LTD.) as an emulsifier dissolved therein, and was used as a measurement sample.

Measurement of the average particle size: The volume-based median size of the measurement samples prepared in the swollen state and dry state was measured with laser diffraction-scattering type particle size distribution measuring device (Microtrac MT-3000, manufactured by NIKKISO CO., LTD.). The average swollen particle size was measured using ion-exchanged water (refraction index 1.333) as a medium, and the average dry particle size was measured using n-hexane having 2 wt % of CRS-75 (refractive index 1.39) dissolved therein. The refractive index of the polyacrylate water-absorbing polymer used was 1.53.

(2) Method for Measuring the Water Absorbency

The water absorbency was calculated from the following equation:

Water absorbency=[weight of the measurement sample after 30 minutes of the start of water absorption (g)−dry weight of the measurement sample (g)]/dry weight of the measurement sample (g).

For the measurement of the water absorbency, the water-absorbing polymer as the measurement sample was swollen sufficiently by adding ion-exchanged water thereto, dispersed in the water for 30 minutes or more to bring the water-absorbing polymer into a water-saturated swollen state, and then weighed. For the measurement of the dry weight, the measurement sample was weighed and dried at 150° C. for 60 minutes in a windless dryer, and the residue was then weighed. The procedure was carried out according to JIS K 0067-1992 (Test methods for loss and residue of chemical products).

(3) Results of the Measurements

Results of the measurements are shown in Table 1.

TABLE 1

| | Polyacrylate water-absorbing polymer | Average swollen particle size (μm) | Average dry particle size (μm) | Water absorbency (g/g) |
|---|---|---|---|---|
| Polymer A | Potassium polyacrylate | 41.0 | 15.0 | 20 |
| Polymer B | Potassium polyacrylate | 88.0 | 30.0 | 25 |
| Polymer C | Ammonium polyacrylate | 32.0 | 15.0 | 10 |
| Polymer D | Ammonium polyacrylate | 81.0 | 30.0 | 20 |
| Polymer E | Sodium polyacrylate | 54.0 | 20.0 | 20 |
| Polymer F | Potassium polyacrylate | 128.0 | 75.0 | 5 |
| Polymer G | Ammonium polyacrylate | 59.0 | 15.0 | 60 |
| Polymer H | Potassium polyacrylate | 31.0 | 25.0 | 2 |
| Polymer I | Potassium polyacrylate | 14.0 | 5.0 | 20 |
| Polymer J | Sodium polyacrylate | 175.0 | 25.0 | 280 |

Example 2

Formulations comprising the Polymers A to J of Example 1 were prepared and evaluated for the effect of unevenness correction of wrinkles and pores and the compatibility with the makeup cosmetic.
(1) Method for Preparing Formulations Each polyacrylate water-absorbing polymer and purified water were weighed out at the ratio in Table 2, and mixed by stirring at room temperature to prepare the formulation.

(2) Sensory Test of Effect of Unevenness correction of Wrinkles and Pores

Using five female subjects, the effect of unevenness correction of wrinkles and pores when applying each formulation of Table 2 to the face was evaluated according to the following scores, and the average of the scores was determined.

3: Unevenness of wrinkles and pores are corrected.
2: Unevenness of wrinkles and pores are slightly corrected.
1: Unevenness of wrinkles and pores are not corrected.

(3) Image Analysis of Effect for Unevenness Correction of Wrinkles

Each formulation of Table 2 was applied to the face of five female subjects, and the change in the number of wrinkles before and after application was measured using the imaging device, VISIA Evolution. The number of wrinkles was calculated based on image analysis. Before the measurement, the subjects had washed their faces with the designated facial wash, and had wiped the face to remove the moisture.

(4) Effect of Unevenness Correction of Pores

Each formulation of Table 2 was applied to the face of five female subjects, and the change in the number of pores before and after application was measured using the imaging device, VISIA Evolution. The number of pores was calculated based on image analysis. Before the measurement, the subjects had washed their faces with the designated facial wash, and had wiped the face to remove the moisture.

(5) Evaluation of Use Feeling

Using five female subjects, the use feeling at the time of application was evaluated according to the following scores, and the average of the scores was determined.

3: Good
2: Slightly good
1: Poor (6) Method for Evaluating Compatibility with Makeup Cosmetic Using five female subjects, the effect of compatibility of each formulation of Table 2 with a liquid foundation when the formulation was applied to the face before the liquid foundation was applied was evaluated according to the following scores, and the average of the scores was determined.

3: Compatible
2: Slightly compatible
1: Not compatible (7) Results of the Evaluation Results of the evaluation are shown in Table 2.

TABLE 2

|   | Content ratio | Sensory test | Number of wrinkles[1] | Number of pores[2] | Use feeling | Compatibility with makeup cosmetic |
|---|---|---|---|---|---|---|
| Inventive formulation 1 | Polymer A: Water = 5:95 | 3.0 | 70.0 | 62.7 | 3.0 | 3.0 |
| Inventive formulation 2 | Polymer A: Water = 7:93 | 3.0 | 67.8 | 61.0 | 2.8 | 2.8 |
| Inventive formulation 3 | Polymer B: Water = 5:95 | 2.5 | 73.2 | 64.3 | 2.5 | 2.5 |
| Inventive formulation 4 | Polymer B: Water = 3:97 | 2.3 | 75.5 | 62.5 | 2.5 | 2.5 |
| Inventive formulation 5 | Polymer C: Water = 5:95 | 2.5 | 74.1 | 63.1 | 2.5 | 2.5 |
| Inventive formulation 6 | Polymer C: Water = 7:93 | 2.7 | 71.6 | 61.8 | 2.3 | 2.3 |
| Inventive formulation 7 | Polymer D: Water = 5:95 | 2.5 | 76.0 | 62.6 | 2.3 | 2.3 |
| Inventive formulation 8 | Polymer E: Water = 5:95 | 3.0 | 69.5 | 62.4 | 3.0 | 3.0 |
| Inventive formulation 9 | Polymer E: Water = 7:93 | 3.0 | 67.5 | 60.9 | 2.8 | 2.8 |
| Comparative formulation 1 | Polymer F: Water = 5:95 | 1.0 | 96.3 | 87.2 | 1.0 | 1.2 |
| Comparative formulation 2 | Polymer G: Water = 5:95 | 2.3 | 97.0 | 88.4 | 2.6 | 1.0 |
| Comparative formulation 3 | Polymer H: Water = 5:95 | 2.6 | 96.8 | 85.6 | 2.4 | 1.9 |
| Comparative formulation 4 | Polymer I: Water = 5:95 | 2.3 | 95.9 | 89.7 | 1.0 | 1.0 |
| Comparative formulation 5 | Polymer J: Water = 5:95 | 1.2 | 98.4 | 90.7 | 2.2 | 1.2 |

[1] Relative value of the number of wrinkles when the number of wrinkles before applying each formulation is taken as 100%

[2] Relative value of the number of pores when the number of pores before applying each formulation is taken as 100%

Applied examples including the water-absorbing polyacrylate polymer according to the present invention are listed below, but the present invention is not intended to be limited thereto. All the cosmetics of Examples 3 to 6 were also evaluated in the same manner as in Example 2, and excellent effects were confirmed.

Example 3

Serum for Unevenness Correction

| | |
|---|---|
| 1. Xanthan gum | 0.4 (% by mass) |
| 2. Hydroxyethylcelluose | 0.1 |
| 3. Polymer E | 5.0 |
| 4. 1,3-Butylene glycol | 5.0 |
| 5. Purified water | q.s. to 100.0 |
| 6. Hydroxyproline | q.s. |
| 7. Purified water | 5.0 |
| 8. Preservative | q.s. |
| 9. Ethanol | 3.0 |

(Preparation Method) Ingredients 1 to 5, 6 and 7, and 8 and 9 are each dissolved at room temperature. While the Ingredients 1 to 5 are stirred, the Ingredients 6 and 7 and Ingredients 8 and 9 are then added thereto. When the uniform mixture is obtained, the preparation is finished.

Example 4

Emulsion for Unevenness Correction

| | |
|---|---|
| 1. Polyoxyethylene POE (20) sorbitan monostearate | 1.0 (% by mass) |
| 2. Polyoxyethylene POE (40) sorbitol tetraoleate | 1.5 |
| 3. Glyceryl monostearate, lipophilic | 1.0 |
| 4. Stearic acid | 0.5 |
| 5. Behenyl alcohol | 1.5 |
| 6. Cetyl palmitate | 0.5 |
| 7. Squalane | 5.0 |
| 8. Cetyl 2-ethyl hexanoate | 5.0 |
| 9. Methyl polysiloxane | 0.5 |
| 10. Preservative | q.s. |
| 11. Polymer A | 6.0 |
| 12. 1,3-Butylene glycol | 7.0 |
| 13. Dipropylene glycol | 4.0 |
| 14. Purified water | q.s. to 100.0 |

(Preparation Method) Both Ingredients 1 to 10 and Ingredients 11 to 14 are warmed and dissolved. While stirring Ingredients 1 to 10 with a homomixer, Ingredients 11 to 14 are gradually added thereto to emulsify the mixture. The mixture is cooled while paddle stirring, and the preparation is finished.

Example 5

Makeup Base for Unevenness Correction

| | |
|---|---|
| 1. NIKKOL NIKKOMULESE LC *[1] | 4.0 (% by mass) |
| 2. Cetearyl alcohol | 1.0 |
| 3. Squalane | 3.0 |
| 4. Phenyl trimethicone | 5.0 |
| 5. Polypropylsilsesquioxane | 2.0 |
| 6. KP-545 *[2] | 1.0 |
| 7. Carbomer | 0.15 |
| 8. Hydroxyethyl acrylate/sodium acryloyldimethyl taurate copolymer | 0.3 |
| 9. Polymer D | 0.1 |
| 10. Chelating agent | q.s. |
| 11. Preservative | q.s. |
| 12. Purified water | q.s. to 100.0 |
| 13. Arginine | 0.05 |
| 14. Purified water | 3.0 |
| 15. 1,3-Butylene glycol | 4.0 |
| 16. Glycerin | 1.0 |
| 17. Pigment grade titanium oxide | q.s. |
| 18. Red iron oxide | q.s. |
| 19. PLASTIC POWDER D-400 *[3] | 3.0 |
| 20. HV45 PM20 *[4] | 3.0 |
| 21. Ethanol | 5.0 |
| 22. Purified water | 5.0 |

*[1] NIKKOL NIKKOMULESE LC (manufactured by Nikko Chemicals Co, Ltd.): cetyl alchohol, stearyl alcohol, behenyl alcohol, phytosterols, glyceryl stearate, PEG-20 phytosterol, hydrogenated lecithin, caprylic/capric triglyceride

*[2] KP-545 (manufactured by Shin-Etsu Chemical Co., Ltd.): alkyl acrylate/dimethicone copolymer, cyclopentasiloxane

*[3] PLASTIC POWDER D-400 (manufactured by Nikko Chemicals Co, Ltd.): HDI/trimethylol hexyllactone crosspolymer, silica

*[4] HV45 PM20 (manufactured by Kobo Products, Inc.): mica, polymethyl methacrylate, titanium oxide (Preparation Method) Ingredients 7 to 12, 13 and 14, 15 to 20, and 21 and 22 are each homogenized at room temperature. Ingredients 1 to 6 and Ingredients 7 to 12 are each warmed and homogeneously mixed and stirred. While stirring Ingredients 7 to 12, Ingredients 13 and 14 are added thereto to homogeneously mix them. While stirring Ingredients 7 to 14, Ingredients 15 to 20 are added thereto to homogeneously mix them. While stirring Ingredients 7 to 20 with a homomixer, Ingredients 1 to 6 are gradually added thereto to emulsify the mixture. The mixture is cooled with stirring, Ingredients 21 and 22 are added thereto at 30° C. to homogenize the mixture, and the preparation is finished.

Example 6

Emulsion-Type Foundation for Unevenness Correction

| | |
|---|---|
| 1. NIKKOL NIKKOMULESE WO *[1] | 5.0 (% by mass) |
| 2. NIKKOL SILBLEND-91 *[2] | 2.5 |
| 3. KSG-15 *[3] | 2.0 |
| 4. Cyclopentasiloxane | 20.0 |
| 5. Dimethicone (6 mPa · s) | 2.5 |
| 6. Diphenylsiloxy phenyl trimethicone | 2.5 |
| 7. KP-545 *[4] | 1.0 |
| 8. Pentaerythrityl tetraethylhexanoate | 2.0 |
| 9. Diisostearyl Malate | 1.0 |
| 10. Siliconized pigment grade titanium oxide | 6.7 |
| 11. Siliconized red iron oxide | q.s. |
| 12. Siliconized yellow iron oxide | q.s. |
| 13. Siliconized black iron oxide | q.s. |
| 14. Polymer B | 0.2 |
| 15. Glycerin | 8.0 |
| 16. 1,3-Butylene glycol | 3.0 |
| 17. sodium chloride | 0.5 |
| 18. Ethanol | 3.0 |

| 19. Chelating agent | q.s. |
| 20. Preservative | q.s. |
| 21. Purified water | q.s. to 100.0 |

*1) NIKKOL NIKKOMULESE WO (manufactured by Nikko Chemicals Co, Ltd.): cyclopentasiloxane, PEG-10 dimethicone, disteardimonium hectorite
*2) NIKKOL SILBLEND-91 (manufactured by Nikko Chemicals Co,, Ltd.): cyclomethicone, dimethicone, dimethicone/vinyl dimethicone crosspolymer
*3) KSG-15 (manufactured by Shin-Etsu Chemical Co., Ltd.): cyclopentasiloxane, dimethicone/vinyl dimethicone Crosspolymer
*4) KP-545 (manufactured by Shin-Etsu Chemical Co., Ltd.): alkyl acrylate/dimethicone copolymer, cyclopentasiloxane (Preparation Method) Ingredients 1 to 13 are stirred with a homomixer to disperse them, Ingredients 14 to 21 are gradually added thereto to emulsify the mixture, and the preparation is finished.

INDUSTRIAL APPLICABILITY

The present invention provides a cosmetic for unevenness correction which conceals wrinkles and pores and has good compatibility with a makeup cosmetic at the time of application.

The invention claimed is:

1. A cosmetic composition for unevenness correction, comprising:
   (a) crosslinked polyacrylate water-absorbing polymer particles comprising one or more monomers selected from the group consisting of acrylic acid, methacrylic acid, 2-acrylamido-2-methylpropanesulfonic acid, 2-methacrylamido-2-methylpropanesulfonic acid, and salts thereof, and one or more crosslinking agents selected from the group consisting of polyethylene glycol diacrylate, ethylene glycol diglycidyl ether, polyethylene glycol diglycidyl ether, and methylenebisacrylamide, wherein the polymer particles:
      (i) have an average swollen particle size in ion-exchanged water of 10 μm to 150 μm and an average dry particle size of 10 μm to 50 μm as measured with a laser diffraction-scattering type particle size distribution measuring device; and
      (ii) have a water absorbency of 5 g/g to 50 g/g; and
   (b) a cosmetic ingredient(s),
   wherein the crosslinked polyacrylate water-absorbing polymer particles are 0.1% to 10.0% by mass of the cosmetic composition.

2. The cosmetic composition for unevenness correction according to claim 1, wherein the cosmetic ingredient(s) comprise an inorganic powder.

3. The cosmetic composition for unevenness correction according to claim 2, wherein the inorganic powder is selected from the group consisting of titanium oxide, mica, hectorite, colcothar, montmorillonite, kaolin, smectite, talc, perlite and iron oxide.

4. The cosmetic composition of claim 1, wherein the one or more monomers are selected from acrylic acid, methacrylic acid and salts thereof.

5. The cosmetic composition of claim 1, wherein the one or monomers are selected from acrylic acid and salts thereof.

6. The cosmetic composition of claim 1, wherein the crosslinked polyacrylate water-absorbing polymer particles are crosslinked potassium polyacrylate water-absorbing polymer particles, crosslinked sodium polyacrylate water-absorbing polymer particles, or crosslinked ammonium polyacrylate water-absorbing polymer particles.

7. A method for correcting skin unevenness comprising (a) applying the cosmetic composition of claim 1 to skin and (b) then applying another cosmetic thereon.

8. A process of making the cosmetic composition of claim 1, comprising combining the crosslinked polyacrylate water-absorbing polymer particles with the cosmetic ingredient(s).

* * * * *